United States Patent
Yamaguchi

(10) Patent No.: US 11,776,799 B2
(45) Date of Patent: Oct. 3, 2023

(54) DATA PROCESSING DEVICE

(71) Applicant: SHIMADZU CORPORATION, Kyoto (JP)

(72) Inventor: Shinichi Yamaguchi, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 17/517,756

(22) Filed: Nov. 3, 2021

(65) Prior Publication Data
US 2022/0059331 A1  Feb. 24, 2022

Related U.S. Application Data

(62) Division of application No. 15/740,954, filed as application No. PCT/JP2015/068961 on Jul. 1, 2015, now Pat. No. 11,222,773.

(51) Int. Cl.
*G06K 9/00* (2022.01)
*H01J 49/00* (2006.01)
(Continued)

(52) U.S. Cl.
CPC ........ *H01J 49/0036* (2013.01); *G01N 33/483* (2013.01); *G06F 17/18* (2013.01);
(Continued)

(58) Field of Classification Search
None
See application file for complete search history.

(56) References Cited

U.S. PATENT DOCUMENTS

2008/0073501 A1* 3/2008 Yamaguchi ............ G16C 20/20
250/282
2011/0127425 A1 6/2011 Kajihara
(Continued)

FOREIGN PATENT DOCUMENTS

CN 102077086 A 5/2011
CN 102194641 A 9/2011
(Continued)

OTHER PUBLICATIONS

Communication dated Dec. 24, 2021 from the China National Intellectual Property Administration in Chinese Application No. 201580081390.2.
(Continued)

*Primary Examiner* — Avinash Yentrapati
(74) *Attorney, Agent, or Firm* — Sughrue Mion, PLLC

(57) ABSTRACT

An analysis operator checks an optical microscopic image obtained with an imaging mass microscope and indicates a color characteristic of an area which the analysis operator is focusing on. An optical microscopic image feature extractor calculates luminance distribution data in the indicated color. An image position adjustment processor performs a position adjustment process on a luminance distribution image derived from the optical microscopic image and an MS imaging graphic, while a resolution adjuster equalizes their spatial resolutions. A statistical analysis processor calculates a coefficient of spatial correlation between the luminance distribution image and the MS imaging graphic for each mass-to-charge ratio. Based on the calculated correlation coefficients, an analysis result display processor extracts a mass-to-charge ratio which shows an ion intensity distribution similar to the luminance distribution image. and displays it on a display unit.

12 Claims, 9 Drawing Sheets

(51) Int. Cl.
     G01N 33/483   (2006.01)
     G16B 40/00    (2019.01)
     G16B 40/30    (2019.01)
     G16B 40/10    (2019.01)
     G06V 10/56    (2022.01)
     G06V 20/69    (2022.01)
     G06T 7/00     (2017.01)
     G06F 17/18    (2006.01)
(52) U.S. Cl.
     CPC ............... *G06T 7/97* (2017.01); *G06V 10/56* (2022.01); *G06V 20/69* (2022.01); *G16B 40/00* (2019.02); *G16B 40/10* (2019.02); *G16B 40/30* (2019.02); *G06T 2207/10056* (2013.01)

(56) References Cited

U.S. PATENT DOCUMENTS

| | | | | |
|---|---|---|---|---|
| 2011/0216952 A1* | 9/2011 | Kajihara | .................. | G06K 9/00 382/128 |
| 2011/0216979 A1* | 9/2011 | Barkol | .................. | G06V 10/75 382/218 |
| 2011/0228970 A1 | 9/2011 | Kajihara et al. | | |
| 2011/0272572 A1* | 11/2011 | Vertes | .................. | H01J 49/04 250/282 |
| 2012/0016598 A1* | 1/2012 | Deininger | .............. | H01J 49/164 702/28 |
| 2012/0133671 A1* | 5/2012 | Setou | .................. | G06T 7/0012 345/593 |
| 2012/0295276 A1* | 11/2012 | Cooks | .................. | H01J 49/0036 435/7.1 |
| 2013/0080072 A1* | 3/2013 | Ikegami | .............. | H01J 49/0004 702/23 |
| 2013/0273560 A1* | 10/2013 | Cooks | .................. | G01N 33/50 435/7.1 |
| 2013/0306857 A1* | 11/2013 | Yamaguchi | ......... | H01J 49/0036 250/281 |
| 2015/0131888 A1* | 5/2015 | Caprioli | .................. | G06K 9/629 382/133 |
| 2015/0380225 A1* | 12/2015 | Yamada | .............. | H01J 49/0036 702/26 |
| 2016/0343558 A1* | 11/2016 | Yamaguchi | ......... | H01J 49/0045 |
| 2017/0271135 A1* | 9/2017 | Yamaguchi | ......... | H01J 49/0036 |
| 2021/0035790 A1* | 2/2021 | Nakakimura | .......... | G01N 27/62 |

FOREIGN PATENT DOCUMENTS

| | | |
|---|---|---|
| CN | 102323363 A | 1/2012 |
| EP | 0 899 569 A2 | 3/1999 |
| JP | 2009-025275 A | 2/2009 |
| JP | 2010-261882 A | 11/2010 |
| JP | 2013-196294 A | 9/2013 |
| JP | 2014-215043 A | 11/2014 |
| JP | 2015-39570 A | 3/2015 |
| WO | 2013/177189 A1 | 11/2013 |

OTHER PUBLICATIONS

Nhu T. N. Phan et al., "Lipid Structural Effects of Oral Administration of Methylphenidate in *Drosophila* Brain by Secondary Ion Mass Spectrometry Imaging", Analytical Chemistry, 2015, pp. 4063-4071, vol. 87.

Communication dated Jul. 3, 2018 from the Japanese Patent Office in counterpart application No. 2017-525740.

Written Opinion dated Oct. 6, 2015 in application No. PCT/JP2015/068961.

Cheng Quan et al., "Discrimination of Quality Grades of Tieguanyin Tea Based on Components Analysis Using Comprehensive Two-dimensional Gas Chromatography—Time-of-flight Mass Spectrometry Coupled with Cluster Analysis and Fisher's Discriminate Analysis", Journal of Instrumental Analysis, 2015, vol. 34, No. 5, pp. 525-531.

Communication dated Feb. 4, 2021, issued by the State Intellectual Property Office of the P.R.C. in application No. 201580081390.2.

"Kenbi Reezaa Raman Wo Mochiita Shuseibun Bunseki Ni Yoru Kemikaru Imeejingu (Chemical Imaging by Principal Component Analysis Using Microscopic Laser Raman)", Thermo Fisher Scientific Inc., <URL: http://www.thermosci.jp/ft-ir-raman/docs/M05005.pdf>.

Yasuto Fujimaki et al., "Improvement of the multivariate analysis technique in microscopic infrared imaging", Bulletin of Tokyo Metropolitan Industrial Technology Research Institute, 2009, pp. 90-91, No. 4.

Cheng Quan et al., "Analysis of the volatile components in Minnan oolong tea by headspace solid phase microextraction coupled with comprehensive two-dimensional gas chromatography-time of flight mass spectrometry and the application in its variety identification", Chinese Journal of Chromatography, Feb. 2015, vol. 33, No. 2, pp. 174-181 (15 pages).

Kiyoshi Ogawa, "Imeejingu Shitsuryou Kenbikyou No Kaihatsu (Development of Imaging Mass Microscope)", Shimadzu Corporation, <URL:http://www.jst.go.jp/pdf/pc201305_shimadzu.pdf>.

Communication dated Jun. 11, 2020, from The China National Intellectual Property Administration in Application No. 201580081390.2.

International Search Report for PCT/JP2015/068961 dated Oct. 6, 2015.

Communication dated May 14, 2018 from the European Patent Office in counterpart application No. 15897153.1.

Office Action dated Sep. 30, 2021 from the China National Intellectual Property Administration in CN Application No. 201580081390.2.

* cited by examiner

OPTICAL MICROSCOPIC IMAGE

MS IMAGING (TIC) GRAPHIC

Fig. 12
(1) REGION OF INTEREST
(2) REGION OF NON-INTEREST
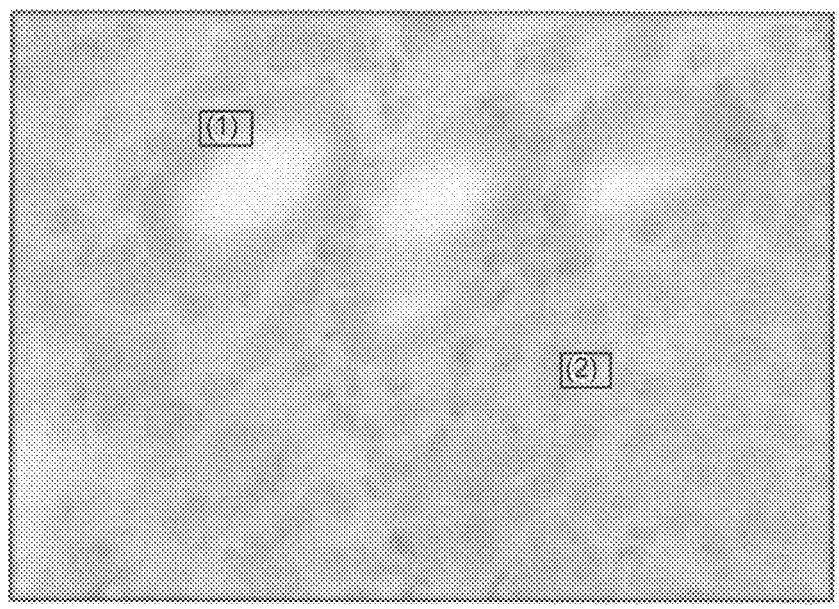
Fig. 13
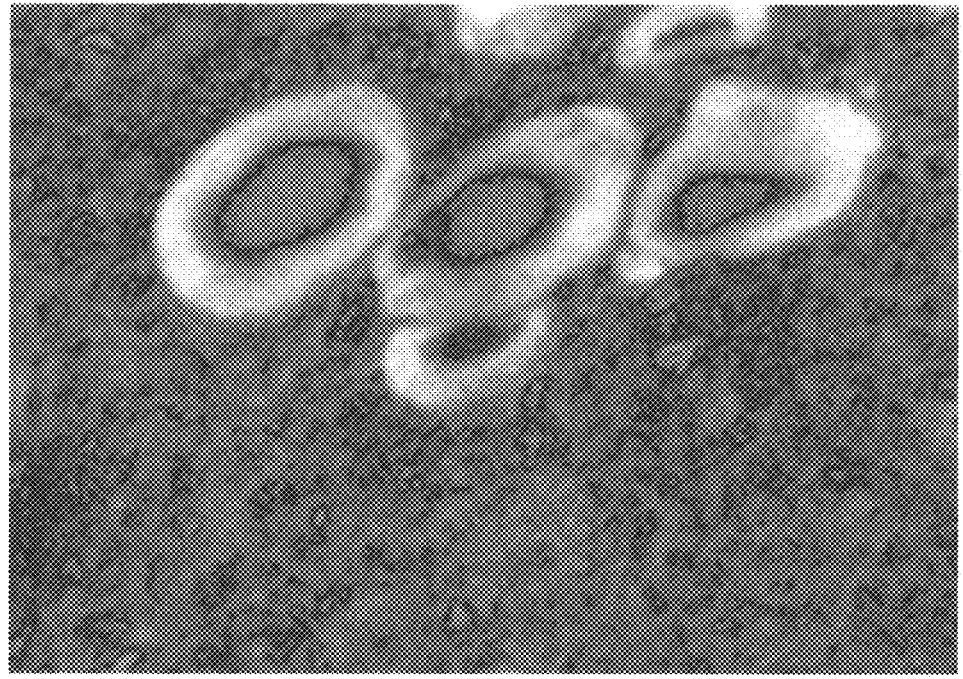

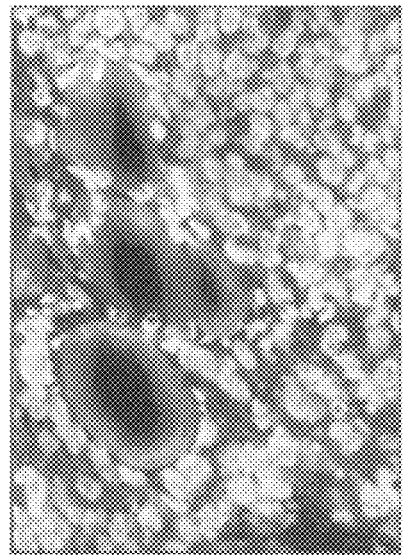
Fig. 14B
FALSE-COLOR COMPOSITE IMAGE
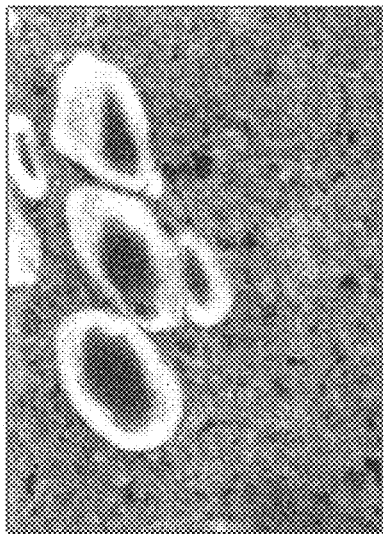
Fig. 14E
SCORE DISTRIBUTION IMAGE FOR PC3
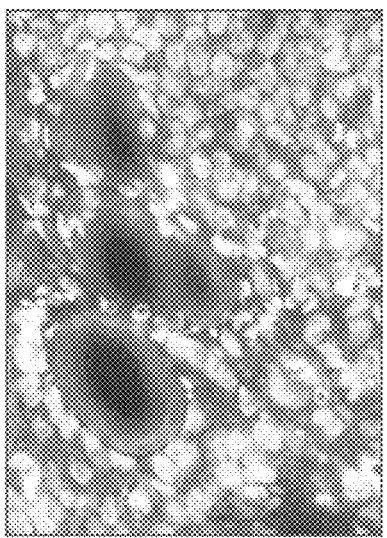
Fig. 14D
SCORE DISTRIBUTION IMAGE FOR PC2
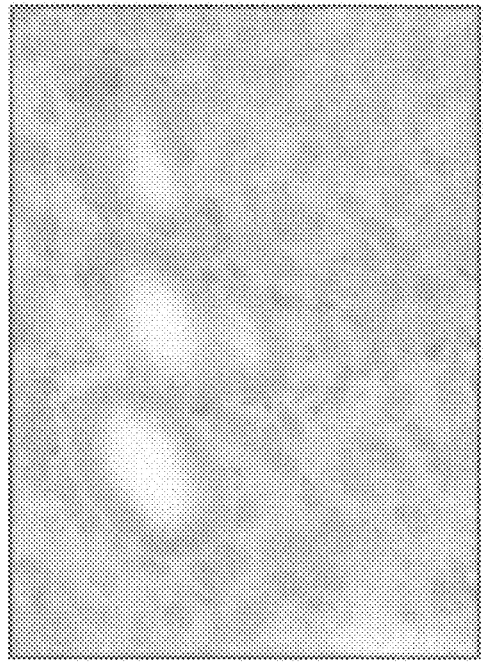
Fig. 14A ORIGINAL IMAGE
Fig. 14C
SCORE DISTRIBUTION IMAGE FOR PC1
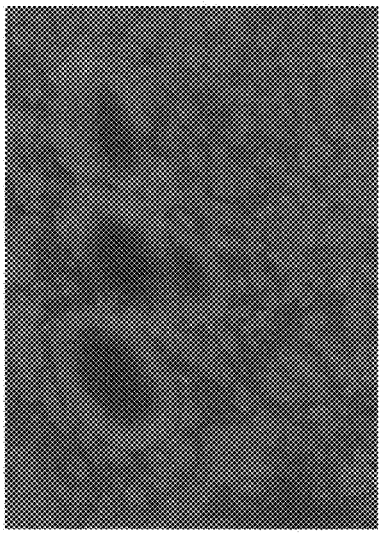

SCORE DISTRIBUTION
IMAGE FOR PC1

SCORE DISTRIBUTION
IMAGE FOR PC2

SCORE DISTRIBUTION
IMAGE FOR PC3

ORIGINAL IMAGE

FALSE-COLOR COMPOSITE IMAGE

DATA PROCESSING DEVICE

CROSS REFERENCE TO RELATED APPLICATIONS

This application is a Divisional Application of U.S. application Ser. No. 15/740,954, filed Dec. 29, 2017, which is a National Stage of International Application No. PCT/JP2015/068961 filed Jul. 1, 2015, the contents of all of which are incorporated herein by reference in their entirety.

TECHNICAL FIELD

The present invention relates to a data processing device for processing data obtained by performing a measurement or observation on a sample or specimen, and more specifically, to a data processing device suitable for acquiring significant information on a sample by processing a plurality of sets of multi-dimensional analysis data (e.g. two-dimensional or three-dimensional data) obtained by different measurement techniques or observation techniques for the same sample.

BACKGROUND ART

Various devices for performing a predetermined measurement or analysis on a sample or specimen to collect data representing a two-dimensional distribution of a predetermined physical quantity for the sample have been commonly known.

For example, an imaging mass microscope disclosed in Non Patent Literature 1 or other documents allows for an observation of the shape and state of the surface of a biological sample or similar specimen through an optical microscope while performing a measurement of a two-dimensional intensity distribution of an ion having a specific mass-to-charge ratio on the same surface of the sample. FIG. 5 is a model diagram illustrating a procedure for obtaining a two-dimensional ion intensity distribution image at a specific mass-to-charge ratio using an imaging mass microscope.

In the imaging mass microscope, a set of mass spectrum data over a specific range of mass-to-charge ratios can be obtained at each of the micro areas 102 formed by subdividing a predetermined two-dimensional area 101 on a sample 100. The collected data are three-dimensional data (mass spectrometric imaging data) which shows the ion intensity with the two-dimensional position information of each micro area 102 and the mass-to-charge ratio information as the parameters. By extracting ion intensities at a desired mass-to-charge ratio from those data, a mapping image showing the two-dimensional ion intensity distribution at that mass-to-charge ratio, i.e. a mass spectrometric imaging graphic, can be created. In general, the intensity distribution of an ion having a specific mass-to-charge ratio shows the distribution of a specific kind of substance. Therefore, based on the mass spectrometric imaging graphic, it is possible to obtain useful information, e.g. the distribution of a biomarker (i.e. a substance related to a specific kind of disease) in a biological tissue.

However, since the amount of data collected in an imaging mass microscope is extremely large, a considerable amount of time and labor is required to locate a mass-to-charge ratio at which the mass spectrometric imaging graphic provides significant information. To address this problem, multivariate analyses have conventionally been used, such as a principal component analysis (PCA), cluster analysis or independent component analysis, to perform an analysis for extracting a mass-to-charge ratio which shows a characteristic two-dimensional distribution, or for searching for a plurality of mass-to-charge ratios which show similar two-dimensional distributions (see Patent Literature 1).

Such analytical techniques using multivariate analyses are not limited to an analysis of data obtained with an imaging mass microscope; they are also commonly used for analyses of data obtained with other types of analyzing devices. For example, Non Patent Literatures 2 and 3 disclose the technique of identifying a substance contained in a sample by performing a principal component analysis on image data obtained by a microscopic infrared imaging method or microscopic laser Raman spectroscopic imaging method.

However, using a multivariate analysis in the previously described manner does not always provide useful information for an analysis operator. One reason for this is that, even when a mass-to-charge ratio showing a singular two-dimensional distribution is located or a plurality of mass-to-charge ratios showing similar two-dimensional distributions are extracted by performing a multivariate analysis on mass spectrometric imaging data (i.e. data of a number of mass spectra) obtained with an imaging mass microscope, the substance corresponding to that two-dimensional distribution is not always the singular substance which is aimed at by the analysis operator. Besides, the optical microscopic image used in the conventional analyzing techniques mentioned earlier merely serves as reference information for helping an analysis operator set an area on a sample within which an imaging mass spectrometric analysis should be performed. Therefore, for example, when a site having a specific shape or color which the analysis operator is focusing on is located on the optical microscopic image, the analysis operator additionally needs to compare two images for each mass-to-charge ratio on the display to locate a mass-to-charge ratio which shows a two-dimensional distribution similar to the distribution of that site. Such a task is extremely cumbersome.

CITATION LIST

Patent Literature

Patent Literature 1: JP 2010-261882 A
Patent Literature 2: JP 2009-25275 A
Patent Literature 3: JP 2014-215043 A

Non Patent Literature

Non Patent Literature 1: Kiyoshi Ogawa, "Imeejingu Shitsuryou Kenbikyou No Kaihatsu (Development of Imaging Mass Microscope)", Shimadzu Corporation, [online], [accessed on May 15, 2015], the Internet Non Patent Literature 2: Yasuto Fujimaki and another author, "Improvement of the multivariate analysis technique in microscopic infrared imaging", *Bulletin of Tokyo Metropolitan Industrial Technology Research Institute*, No. 4, 2009, [online], [accessed on May 15, 2015], the Internet Non Patent Literature 3: "Kenbi Reezaa Raman Wo Mochiita Shuseibun Bunseki Ni Yoru Kemikaru Imeejingu (Chemical Imaging by Principal Component Analysis Using Microscopic Laser Raman)", Thermo Fisher Scientific Inc., [online], [accessed on May 15, 2015], the Internet

SUMMARY OF INVENTION

Technical Problem

The present invention has been developed to solve the previously described problem. Its primary objective is to provide a data processing device capable of acquiring useful information that cannot be obtained by conventional analyzing techniques, by performing an analyzing process in which a plurality of sets of data obtained through different kinds of measurements, observations or the like are compared with or associated with each other.

Solution to Problem

A data processing device according to the first aspect of the present invention developed for solving the previously described problem is a data processing device for processing first image data obtained for a two-dimensional area on a sample by a first measurement technique and second image data obtained for a two-dimensional area on the same sample by a second measurement technique different from the first measurement technique, to obtain information on the sample, the data processing device including:
  a) a preprocessor for performing a position adjustment process on the first image data and the second image data so that pixels at which measurement results for the same site on the sample appear are located at corresponding positions on both images, and for performing a data conversion process for equalizing the spatial resolution between the first and second image data; and
  b) a statistical analysis processor for performing a statistical analysis process on the data at the pixels which spatially correspond to each other in the first and second image data after the adjustment of the spatial position and the equalization of the spatial resolution are performed by the preprocessor, to calculate an index value indicating the degree of similarity or difference in the two-dimensional signal intensity distribution between the first and second image data.

Each of the first and second measurement techniques may be any of the various kinds of measurements and analyses, such as a mass spectrometric imaging measurement, Raman spectroscopic measurement, fluorescence measurement, emission-intensity or absorption measurement of electromagnetic waves at various wavelengths (terahertz region, near or far infrared region, visible region, ultraviolet region, X-ray region, etc.), PET (positron emission tomography) measurement, MRI (magnetic resonance imaging) measurement, ESR (electron spin resonance) measurement, CT (computed tomography) measurement, surface analysis using EPMA (electron probe microanalyzer), as well as an observation with an electron microscope or optical microscope. The size of the individual pixels forming the image data is expected to be within a range from a minimum value of approximately 1 $nm^2$ to a maximum value of approximately 1 $m^2$.

For example, when the data processing device according to the first aspect of the present invention is applied to an imaging mass microscope mentioned earlier, an observation with an optical microscope can be used as the first measurement technique, while a mass spectrometric imaging measurement can be used as the second measurement technique. An optical microscopic measurement normally yields a colored sample-surface image, in which case a set of data forming a sample-surface image having a specific color (wavelength) component can be used as the first image data. Specifically, if a site or area which the analysis operator is focusing on in an optical microscopic image has a characteristic color different from the other areas, a set of data forming an image having that color component, i.e. an image showing the luminance distribution of that color, can be used as the first image data. Meanwhile, in the mass spectrometric imaging measurement, an image which shows an ion intensity distribution is obtained for each mass-to-charge ratio, and a set of data forming those images can be used as the second image data. That is to say, the first and second data may be a set of data forming a plurality of images and do not need to be a set of data forming a single image.

If a mass spectrometric imaging measurement employing an $MS^n$ measurement with n being equal to or greater than two is used as the second measurement technique, it is possible to use, as the processing target, image data which shows a two-dimensional distribution of an intended component, such as a fragment originating from a specific compound, while avoiding influences of foreign substances.

In the data processing device according to the first aspect of the present invention, when the statistical analysis processor performs the statistical analysis process, it is necessary that the pixels at which the measurement results for the same site on the sample appear should be located roughly at the same position in both first and second image data. Additionally, both image data should have the same spatial resolution; i.e. the size of the micro area on the sample reflected in one pixel should be the same. Accordingly, if the pixels for the same site on the sample are not located at corresponding positions on the two images, the preprocessor performs an appropriate position adjustment process, such as the scaling, rotation and/or transformation of one of the two images. If there is a discrepancy of the spatial resolution, the preprocessor performs a data conversion process for decreasing or increasing (interpolating) the spatial resolution of one of the two images. Consequently, a definite, pixel-to-pixel correspondence is established between the image created from the first image data and the one created from the second image data.

In the previously described case of using an optical microscopic image and mass spectrometric imaging graphic, the optical microscopic image normally has a higher spatial resolution. In that case, the preprocessor can decrease the spatial resolution of the data forming the optical microscopic image to equalize the spatial resolution between the optical microscopic image data and the mass spectrometric imaging data.

Subsequently, the statistical analysis processor calculates an index value which indicates the degree of similarity or difference in the two-dimensional signal intensity distribution between the first image data and the second image data by performing a statistical analysis process on the data for the pixels which spatially correspond to each other, i.e. which are related to the same position on the sample. The simplest statistical analysis process available for such a purpose is a correlation analysis in which the correlation coefficient between the two sets of image data is calculated. It is also possible to use a multivariate analysis which is effectively a technique for determining the degree of correlation, such as a partial least squares (PLS) or discriminant analysis.

In the data processing device according to the first aspect of the present invention, for example, even when the amount of second image data (the number of images) is extremely large, it is easy to find an image created from the second image data and showing a signal intensity distribution similar to a characteristic signal intensity distribution on an image created from the first image data, e.g. an optical microscopic image, based on the index value obtained through the statistical analysis process in the previously described manner.

In a preferable mode of the data processing device according to the first aspect of the present invention, the second image data includes data forming a plurality of images obtained under different values of a parameter, and the statistical analysis processor extracts a value of the parameter at which an image having a high degree of similarity to or difference from the two-dimensional signal intensity distribution in one image created from the first image data is obtained.

In the case where the second image data are mass spectrometric imaging data, the aforementioned parameter is mass-to-charge ratio. This configuration makes it possible, for example, to extract a mass-to-charge ratio at which the two-dimensional distribution of the signal intensity has a similar appearance to the distribution of a specific site or area in the optical microscopic image. A substance corresponding to the site or area which the analysis operator is focusing on in the optical microscopic image can also be investigated if it is possible to identify the substance from the mass-to-charge ratio using a database search or other methods.

In the case of performing a statistical analysis process using a correlation coefficient in the previously described manner, the statistical analysis processor can calculate, for each of a plurality of images created from the second image data, the correlation coefficient between one image created from the first image data and one image created from the second image data, and extract a value of the parameter at which an image having a high degree of similarity or difference in the two-dimensional signal intensity distribution is obtained based on the correlation coefficient.

In the case of using a multivariate analysis for the statistical analysis process, a set of image data forming a plurality of images can be processed at one time. Therefore, the statistical analysis processor can perform a multivariate analysis on the first image data and the second image data, and extract a value of the parameter at which an image having a high degree of similarity or difference in the two-dimensional signal intensity distribution is obtained based on the result of the multivariate analysis.

As with the second image data, the first image data may also include data forming a plurality of images obtained under different values of a parameter. For example, a colored optical microscopic image can be divided into a plurality of sample-surface images having different color components. Accordingly, the color or wavelength can be considered as a parameter. In this case, a combination of the value of a parameter in the first measurement technique and the value of a parameter in the second measurement technique which have two-dimensional signal intensity distributions similar to or different from each other can be extracted by using a multivariate analysis in the statistical analysis process.

A data processing device according to the second aspect of the present invention developed for solving the previously described problem is a data processing device for processing sample spectrum data obtained for each of a plurality of micro areas within a two-dimensional area on a sample and reference spectrum data provided as a reference, to obtain information on the sample, the data processing device including:

a) a statistical analysis processor for performing, for each of the micro areas, a statistical analysis process on the sample spectrum data corresponding to the micro area and the reference spectrum data, to calculate an index value indicating the degree of similarity or difference between spectra; and b) an image creator for creating an image showing a two-dimensional distribution of the index value corresponding to the two-dimensional area on the sample, based on the index value obtained for each of the micro areas by the statistical analysis processor.

Representative examples of the spectrum include: a mass spectrum with one axis representing the mass-to-charge ratio obtained by a mass spectrometer; and a spectrum with one axis representing the wavelength or wavenumber, or energy level, obtained by an emission-intensity measurement or absorption measurement of electromagnetic waves. If a mass spectrum obtained by an $MS^n$ measurement with n being equal to or greater than two is used as the spectrum, it is possible to obtain a process result based on an $MS^n$ spectrum for a desired component, such as a fragment originating from a specific compound, while avoiding influences of foreign substances. It should be noted that the spectrum does not need to be one directly obtained by such measurements. For example, as described in the international application No. PCT/JP2014/082384 filed by the applicant, when a multivariate analysis, such as a principal component analysis, is performed on mass spectrometric imaging data, factor loadings for each principal component can be determined. Since the factor loading is determined for each mass-to-charge ratio, a "factor-loading spectrum" can be created, which shows the relationship between mass-to-charge ratio and factor loading in a manner similar to a mass spectrum. Accordingly, this factor-loading spectrum can be used as the reference spectrum data, while a mass spectrum obtained by a measurement can be used as the sample spectrum data.

When the data processing device according to the second aspect of the present invention is applied to an imaging mass microscope, and a mass spectrum corresponding to a known kind of substance is used as the reference spectrum data, the image creator can create an image showing an area in which the known substance is likely to be present. When the data processing device according to the second aspect of the present invention is applied in an imaging mass microscope, and a factor-loading spectrum for an appropriate principal component obtained by performing a principal component analysis on mass spectrometric imaging data is used as the reference spectrum data, the image creator can create an image showing the distribution of a degree of similarity in chemical structure between a substance which characterizes an overall mass spectrum of a two-dimensional area on a sample subjected to the measurement and a substance which is present at each pixel.

A data processing device according to the third aspect of the present invention developed for solving the previously described problem is a data processing device for processing first image data obtained for a two-dimensional area on a sample by a first measurement technique and second image data obtained for a two-dimensional area on the same sample by a second measurement technique different from the first measurement technique, to obtain information on the sample, the data processing device including:

a) a principal component analysis executer for performing a principal component analysis on the first image data to obtain score-value distribution data showing a two-dimensional distribution of score values for each principal component, and for similarly performing a principal component analysis on the second image data to obtain score-value distribution data showing a two-dimensional distribution of score values for each principal component; and b) an associated principal component extractor for spatially comparing the score-value distribution data for a principal component based on the first image data and the score-value distribution data for a principal component based on the second image data obtained by the principal component analysis executer, to extract a combination of principal components having a high spatial correlation.

In the data processing device according to the third aspect of the present invention, for example, a set of data forming an optical microscopic image mentioned earlier, or a set of data obtained by emission-intensity measurements or absorption measurements of electromagnetic waves at various wavelengths, can be used as the first image data, while mass spectrometric imaging data can be used as the second image data. In that case, the correlation between a principal component determined by a principal component analysis on an optical microscopic observation or optical measurement and a principal component determined by a principal component analysis on a mass spectrometric imaging measurement can be investigated. Therefore, for example, it is possible to compare factor-loading spectra of highly correlated principal components with each other, and estimate a characteristic substance from both mass-to-charge ratio and wavelength or energy level.

A data processing device according to the fourth aspect of the present invention developed for solving the preciously described problem is a data processing device for processing first image data including data forming a plurality of images obtained for a two-dimensional area on a sample by a predetermined measurement technique under different values of a first parameter, and second image data including data forming a plurality of images obtained for a two-dimensional area different from the aforementioned two-dimensional area on the same sample or a two-dimensional area on a different sample by the predetermined measurement technique under different values of a second parameter, to obtain information on one or a plurality of samples, the data processing device including:

a) a principal component analysis executer for performing a principal component analysis on the first image data to obtain a factor-loading spectrum showing the relationship between the first parameter and the factor loading for each principal component, and for performing a principal component analysis on the second image data to obtain a factor-loading spectrum showing the relationship between the second parameter and the factor loading for each principal component; and b) an associated principal component extractor for comparing the factor-loading spectrum of each of the principle components based on the first image data and the factor-loading spectrum of each of the principle components based on the second image data, to extract a combination of principal components having a high spectral correlation.

In the data processing device according to the fourth aspect of the present invention, the measurement technique for obtaining the first image data is the same as the one used for obtaining the second image data. Besides, in the present case, the sample for which the first image data are obtained may be the same as or different from the sample for which the second image data are obtained. In any case, if there is a high correlation between the factor-loading spectrum of a principal component based on the first image data and that of a principal component based on the second image data, it is possible to compare the two-dimensional distributions of the score values for those principal components.

Advantageous Effects of the Invention

With the data processing device according to the present invention, useful information on a sample can be collected for identifying a substance contained in the sample, grasping the two-dimensional distribution of the substance, and determining the quantity of the identified substance. Specifically, for example, the data processing device according to the present invention conveniently allows for an investigation of the mass-to-charge ratio of a substance singularly present at a site or area having a color which the analysis operator is focusing on in an optical microscopic image, whereby the substance showing a two-dimensional distribution which the analysis operator is focusing on can be easily and accurately identified.

BRIEF DESCRIPTION OF DRAWINGS

FIG. 12 is one example of an optical microscopic image of a piece of tissue sampled from a living organism and stained with HE.

FIG. 13 is an image obtained by converting the image shown in FIG. 12 into a monochromatic image based on the color of a region of interest and that of a region of non-interest.

FIG. 14A is an original optical microscopic image, FIGS. 14C through 14E are distribution images of the score values for each principal component obtained by performing a principal component analysis on the original image, and FIG. 14B is a false-color composite image created from those distribution images.

DESCRIPTION OF EMBODIMENTS

Embodiments of the data processing device according to the present invention are hereinafter described with reference to the attached drawings.

First Embodiment

Figure 1:
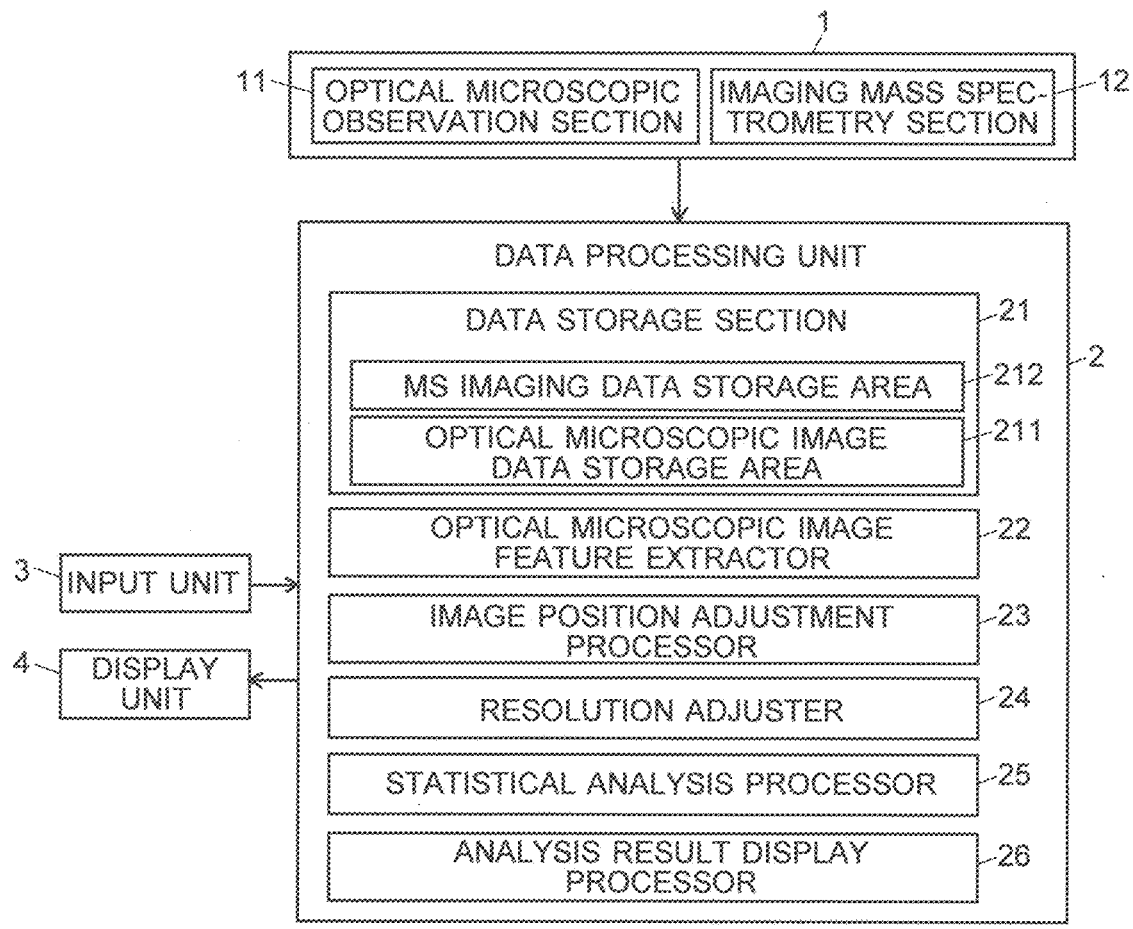
FIG. 1 is a schematic configuration diagram of the first embodiment of an imaging mass microscope system using a data processing device according to the present invention.

FIG. 1 is a schematic configuration diagram of the first embodiment of an imaging mass microscope system using a data processing device according to the present invention.

This system includes an imaging mass microscope main unit 1 and a data processing unit 2.

The imaging mass microscope main unit 1 includes: an optical microscopic observation section 11 for obtaining an optical microscopic observation image of a two-dimensional area on a sample; and an imaging mass spectrometry section 12 for performing a mass spectrometric analysis over a predetermined range of mass-to-charge ratios for each of the micro areas formed by subdividing a predetermined two-dimensional area on the same sample, to collect mass spectrum data for each micro area.

The data processing unit 2 includes the following functional blocks: a data storage section 21, which has an optical microscopic image data storage area 211 for storing optical microscopic image data and an MS imaging data storage area 212 for storing mass spectrometric imaging data; an optical microscopic image feature extractor 22; an image position adjustment processor 23; a resolution adjuster 24; a statistical analysis processor 25; and an analysis result display processor 26. An input unit 3 for allowing users to enter various parameters and issue commands for the data processing, as well as a display unit 4 for displaying various obtained images and analysis results, are connected to the data processing unit 2.

The data processing unit 2 can be constructed using a personal computer as a hardware resource, with the functions of the aforementioned sections realized by executing, on the personal computer, a dedicated processing software program previously installed on the same computer.

Figure 5:
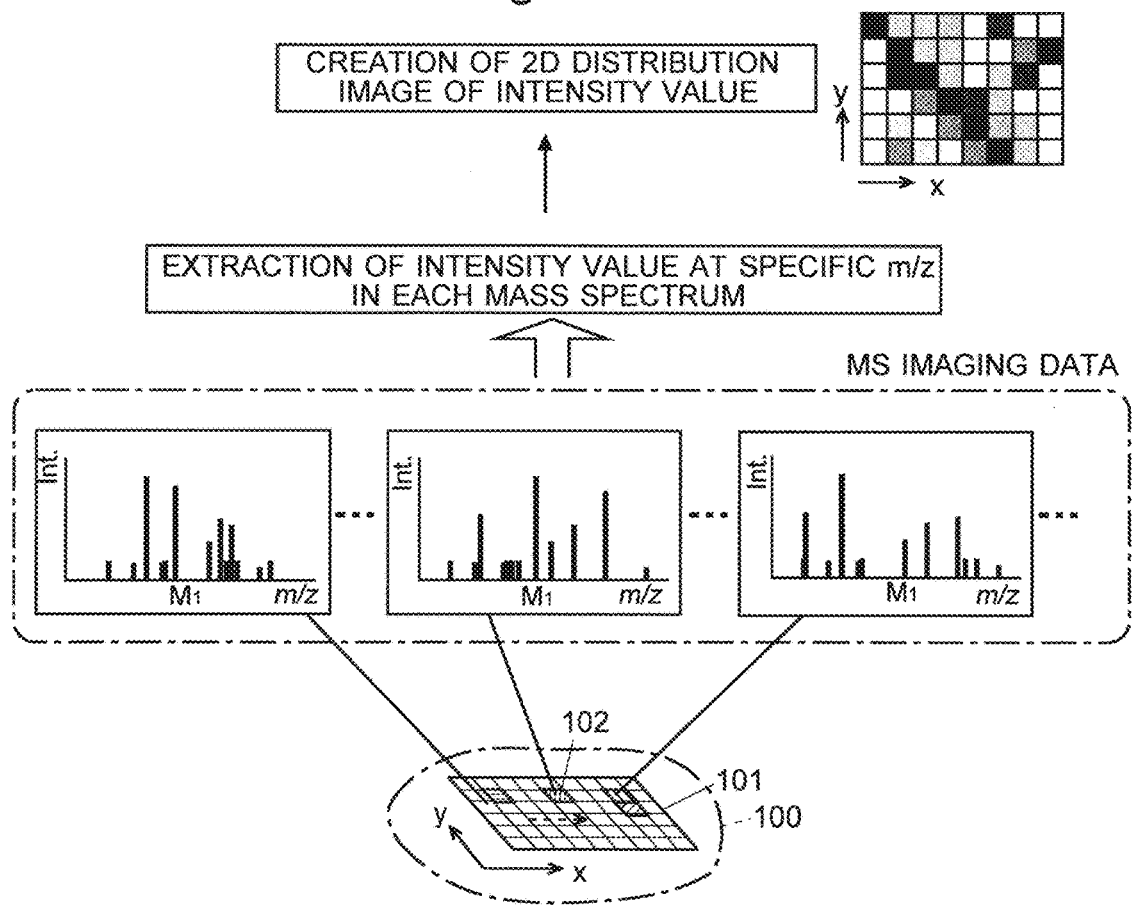
FIG. 5 is a model diagram for explaining the procedure for obtaining a two-dimensional ion intensity distribution image at a specific mass-to-charge ratio by using an imaging mass microscope.

In the imaging mass microscope main unit 1, a sample is set, such as a slice of biological tissue taken from a living organism. In the optical microscopic observation section 11, which includes an optical microscope and an imaging unit, an optical microscopic image of the sample surface is taken, and the thereby obtained image data are sent to the data processing unit 2 and stored in the optical microscopic image data storage area 211 of the data storage section 21. On the other hand, though not shown, the imaging mass spectrometry section 12 includes an ion source employing a laser desorption ionization method, a time-of-flight mass analyzer and other devices. As shown in the already described FIG. 5, each micro area (which corresponds to one pixel) 102 formed by subdividing a predetermined two-dimensional area 101 on a sample 100 is irradiated with laser light to ionize components present on the micro area 102. The generated ions are separated according to their mass-to-charge ratios and detected to obtain mass spectrum data. Mass spectrum data obtained at each of the large number of micro areas 102 are sent to the data processing unit 2 and stored in the MS imaging data storage area 212 of the data storage section 21.

In the imaging mass spectrometry section 12, when needed, an $MS^n$ measurement with n being equal to or greater than two is performed for each micro area 102 to collect $MS^n$ spectrum data. Accordingly, the mass spectrum data to be stored in the MS imaging data storage area 212 may be $MS^n$ spectrum data.

Figure 2A:
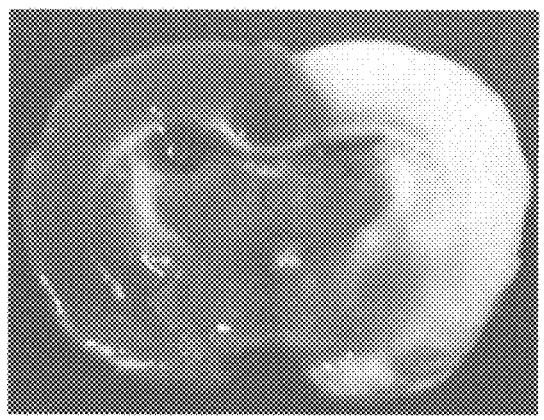
FIGS. 2A and 2B show one example of the images to be subjected to the data processing operation in the imaging mass microscope system according to the first embodiment.
Figure 2B:
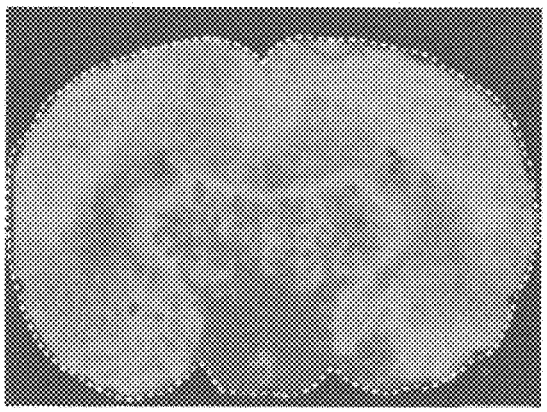
Figure 3:
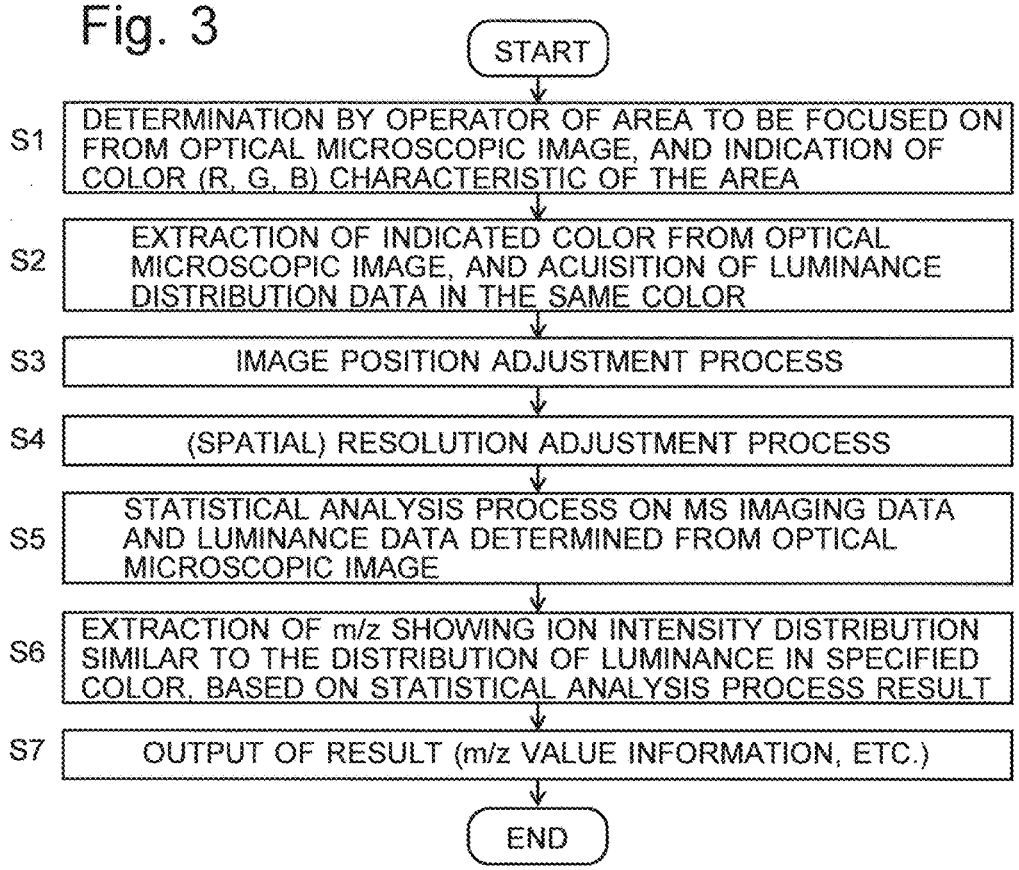
FIG. 3 is a flowchart showing the data processing operation in the imaging mass microscope system according to the first embodiment.
Figure 4:
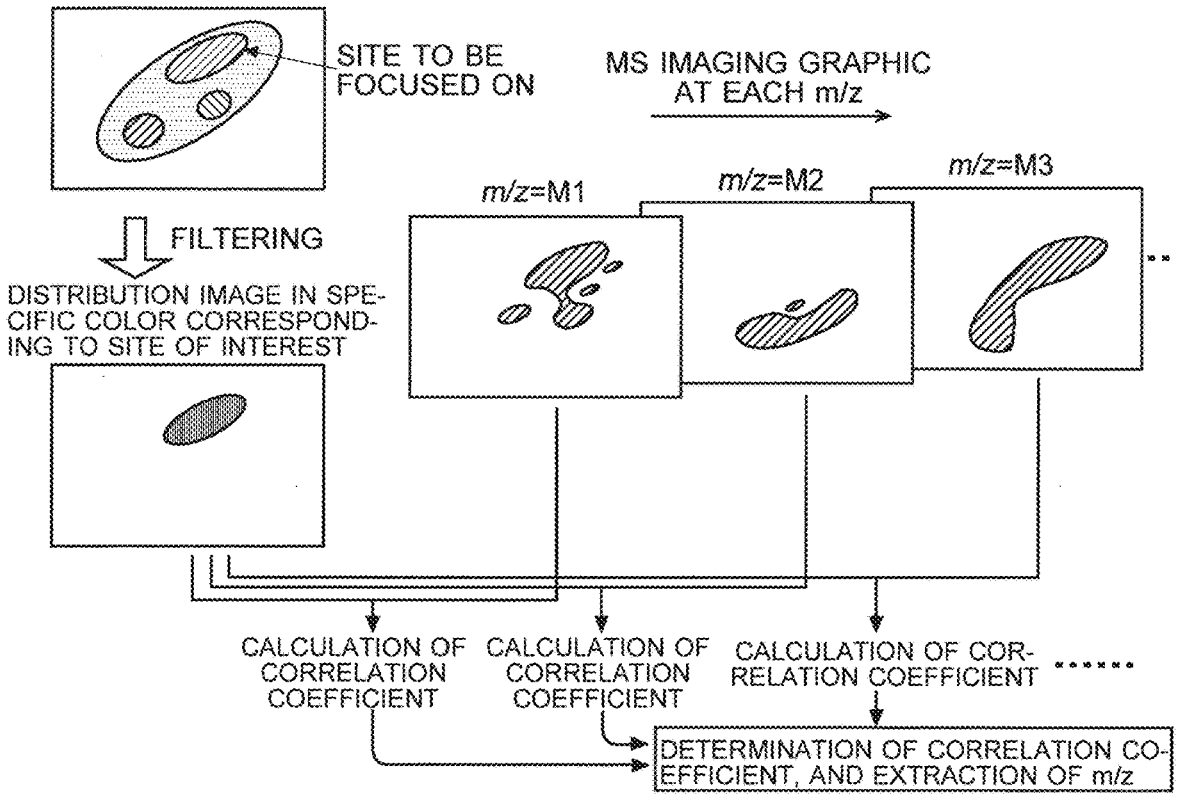
FIG. 4 is a model diagram for explaining the data processing operation shown in FIG. 3.

FIG. 2A is one example of an optical microscopic image of a biological sample, and FIG. 2B is an image of a mass spectrometric imaging graphic created from total ion current signals (TIC) obtained by performing an imaging mass spectrometric analysis on the same biological sample. This biological sample is a piece of brain tissue sampled from a model mouse of cerebral infarction. Under the condition that the data forming such images are stored in the data storage section 21, the data processing unit 2 performs characteristic processing operations, which will be hereinafter described with reference to FIGS. 3 and 4. FIG. 3 is a flowchart showing the flow of the data processing operation in the system of the present embodiment, while FIG. 4 is a model diagram for explaining the data processing operation.

Initially, when an analysis operator performs a predetermined operation on the input unit 3, the optical microscopic image feature extractor 22 reads the data corresponding to the specified optical microscopic image from the optical microscopic image data storage area 211, reproduces the optical microscopic image, and displays it on the screen of the display unit 4. Viewing the displayed optical microscopic image, the analysis operator determines an area or site to be focused on, selects a specific color characteristic of that area or site from the primary colors of RGB (i.e. R, G or R) or other colors, and indicates the color from the input unit 3 (Step S1). In the example shown in FIG. 2A, either the site where the blood flow is blocked due to the cerebral infarction (the white portion on the right side in FIG. 2A), or the site where the blood flow is still secured (the left portion in FIG. 2A; this portion will be shown in red in a colored image) is the site to be focused on.

Next, the optical microscopic image feature extractor 22 performs an appropriate optical filtering process on the optical microscopic image to calculate distribution data of the luminance value in the primary color characteristic of the area being focused on (Step S2). For example, if the area being focused on is the site where the blood flow is still secured, an optical filtering process for selectively extracting the red portion is performed to obtain data of the luminance value in the red color at each pixel. From these data, an image showing the distribution of the color corresponding to the site being focused on (this image is hereinafter called the "specific color luminance distribution image") can be created, as shown in FIG. 4.

Another actual example of the processes of Steps S1 and S2 is hereinafter given. FIG. 12 is an optical microscopic image of a piece of tissue sampled from a living organism and stained with hematoxylin and eosin (HE). Suppose that the analysis operator has specified the site labelled "(1)" in the image as the region of interest, and the area labelled "(2)" as the region of non-interest (though unclear in FIG. 12, there is a difference in the tissue color between the region of interest and the region of non-interest). Based on the color difference between the region of interest and the region of non-interest, the optical microscopic image feature extractor 22 converts the image into a monochromatic image in such a manner that a pixel whose color is closer to the region of interest will be brighter while a pixel whose color is closer to the region of non-interest will be darker. FIG. 13 shows the thereby obtained image, in which the region of interest is clearly shown. This image can be used as the specific color luminance distribution image.

If the characteristic color of the area or site to be focused on is unknown, or if the color difference on the optical microscopic image is difficult to visually recognize, a principal component analysis or similar multivariate analysis may be used to determine a characteristic color of the area or site to be focused on, or to convert the image so that the color difference will be clearer.

FIGS. 14A-14E and 15A-15E show examples of such a processing method. Specifically, FIGS. 14A-14E show an example in which the optical microscopic image of the HE-stained tissue shown in FIG. 12 was processed, while FIGS. 15A-15E show an example in which the optical microscopic image of the piece of brain tissue of a model mouse of cerebral infarction shown in FIG. 2 was processed. In each set of figures, FIG. 14A/15A shows the original image, while FIGS. 14C-14E/15C-15E respectively show the distributions of the score values for the first through third principal components (PC1-PC3) determined by performing a principal component analysis on the data of the pixels forming the original image. FIG. 14B/15B shows an image obtained by synthesizing the distribution images of the score values for PC1-PC3 after assigning the colors of R, G and B to those images, respectively. In this false-color composite image, the sites which have similar colors in the original image can be seen in clearly different colors. The optical microscopic image feature extractor 22 creates such a false-color image and displays it on the display unit 4, thereby allowing the analysis operator to easily locate an area or site to be focused on.

Subsequently, the image position adjustment processor 23 performs a position adjustment process for correcting the size, orientation, distortion and other properties of the image of the same target on the optical microscopic image and the mass spectrometric imaging graphic (Step S3). For example, this process is performed as follows: Using the specified optical microscopic image as the reference, the mass spectrometric imaging graphic is scaled, rotated, and/or deformed according to a predetermined algorithm so that the positional relationship on the sample becomes roughly the same on both images. A mass spectrometric imaging graphic created from the TIC as shown in FIG. 2B should preferably be used as the mass spectrometric imaging graphic in the present process, although a mass spectrometric imaging graphic at an appropriate mass-to-charge ratio may also be used. In place of the optical microscopic image, the mass spectrometric imaging graphic may also be used as the reference, in which case the optical microscopic image should be used to calculate the quantities for the positional adjustment, and the specific color luminance distribution image should be scaled, rotated and/or deformed according to those adjustment quantities. For such an image position adjustment process, for example, the technique described in Patent Literature 1 can be used.

The (positional) resolution of an optical microscopic image is normally determined by the resolving power of the imaging camera, whereas the resolution of a mass spectrometric imaging graphic is determined by the spot size of a laser beam delivered onto the sample to ionize the sample. Therefore, it is often the case that the resolution of the mass spectrometric imaging graphic is lower than that of the optical microscopic image. For the calculating process which will be described later, the two images should preferably have the same positional resolution. Therefore, the resolution adjuster 24 performs a resolution adjustment process for equalizing the resolution of the two images (Step S24).

A simple method for equalizing the resolution is to decrease the resolution of the higher-resolution image to that of the lower-resolution image. For example, the binning process is useful as such a method. It is also possible to increase the resolution of the lower-resolution image to that of the higher-resolution image. This can be achieved by initially performing an up-sampling process on the lower-resolution image to apparently equalize the number of pixels, and subsequently performing an interpolation process on each pixel using a plurality of adjacent or nearby pixels to calculate the pixel values for filling the pixels newly inserted by the up-sampling process. For example, a technique described in Patent Literature 2 or 3 can be used for such a resolution adjustment process using the interpolation.

After the image position adjustment process and the resolution adjustment process have been performed in the previously described manner, the pixels located at the same two-dimensional position can be related to each other between the specific color luminance distribution image created from the optical microscopic image and the mass spectrometric imaging graphic. The statistical analysis processor 25 applies an appropriate statistical analysis technique to the mass spectrometric imaging data and the luminance data forming the specific color luminance distribution image after the image position adjustment process and the resolution adjustment process, to search for a mass-to-charge ratio which shows a two-dimensional distribution similar to the specific color luminance distribution image (Step S5). The simplest technique of the statistical analysis available for this purpose is the correlation analysis using a correlation coefficient.

More specifically, the ion intensity distribution on a mass spectrometric imaging graphic at a mass-to-charge ratio can be expressed by one vector m in a multi-dimensional space whose number of dimensions is equal to the total number of pixels. Similarly, the distribution of the luminance value in the specific color luminance distribution image can be expressed by one vector r in the multi-dimensional space whose number of dimensions is equal to the total number of pixels. Based on the two vectors m and r in the multi-dimensional space, a correlation coefficient between the two images can be calculated. As shown in FIG. 4, the correlation coefficient is calculated for each mass spectrometric imaging graphic obtained at a different mass-to-charge ratio. A correlation coefficient having a positive value closer to 1 means that the ion intensity distribution at the mass-to-charge ratio concerned is closer to the distribution of the luminance value. A correlation coefficient having a negative value closer to −1 means that the ion intensity distribution at the mass-to-charge ratio concerned is closer to the inversion of the distribution of the luminance value.

The statistical analysis processor 25 compares the correlation coefficient calculated for each mass-to-charge ratio in the previously described manner with a threshold and extracts a mass-to-charge ratio which shows an ion intensity distribution close to the distribution of the luminance value (Step S6). The analysis result display processor 26 displays one or more mass-to-charge ratios extracted in Step S6 as the analysis result on the screen of the display unit 4 (Step S7). It is also possible to create a mass spectrometric imaging graphic at the extracted mass-to-charge ratio and display it on the screen of the display unit 4.

Thus, the imaging mass microscope system in the first embodiment can extract a mass-to-charge ratio which shows an ion intensity distribution similar to the shape of a site or area which an analysis operator is focusing on in an optical microscopic image, and present the analysis operator the mass-to-charge ratio and/or a mass spectrometric imaging graphic at that mass-to-charge ratio. Additionally, a compound corresponding to that mass-to-charge ratio may also be determined, for example, by a database search, and the compound and/or other items of information concerning the compound may be displayed.

Conversely, the system can also extract a mass-to-charge ratio which shows an ion intensity distribution dissimilar to the shape of the site or area which the analysis operator is focusing on in the optical microscopic image, as well as identify and display a compound corresponding to that mass-to-charge ratio.

In the previous description, a technique which utilizes a simple correlation coefficient is used as the statistical analysis technique in Step S5. A multivariate analysis may also be used, such as the partial least squares (PLS). For example, when the PLS is used, a set of luminance data which form one image based on an optical microscopic image and a set of data which form one of a large number of mass spectrometric imaging graphics are each represented in a matrix form, and a score is calculated by a known PLS method. The PLS score represents the correlation between the two sets of image data, with one of those sets of data as the training data. Accordingly, an appropriate mass-to-charge ratio can be selected based on a set of data that gives a high score. A multivariate analysis different from the PLS can also be used if the analysis yields an index value which indicates the correlation.

In the first embodiment, two-dimensional data of a luminance distribution image in a specific color obtained from an optical microscopic image are compared with three-dimensional data of an ion intensity distribution image at each mass-to-charge ratio, and a mass-to-charge ratio whose distribution is similar to the distribution in the two-dimensional data is extracted. A similar process can also be performed on various kinds of two-dimensional data other than the aforementioned one if the data have been obtained for the same area on the same sample.

Examples of the two-dimensional data include: data showing the distribution of the degree of absorption or radiation intensity of a specific wavelength of light, X-rays or other electromagnetic waves; data showing the intensity distribution of Raman-scattered light or fluorescent emission, or stained image data; data of an image taken by PET (positron emission tomography), CT (computed tomography), MRI (magnetic resonance imaging), ESR (electron spin resonance), or other techniques; image data obtained by utilizing the radioactive isotope labelling; image data using the radioactive isotope labelling; and surface asperity image data obtained with EPMA or SPM (scanning probe microscope). As for the three-dimensional data, for example, a number of sets of data which show the degree of absorption of light at various wavelengths may be used in place of the mass spectrometric imaging data.

In particular, when analyzing a slice of biological tissue or the like in the aforementioned manner, it is advantageous to use an image obtained by fluorescently labelling the sample as the optical microscopic image of the sample, while using mass spectrometric imaging data obtained by an $MS^n$ measurement with n being equal to or greater than two as the three-dimensional data. The use of mass spectrometric imaging data obtained by an $MS^n$ measurement with n being equal to or greater than two as the three-dimensional data in place of mass spectrometric imaging data obtained by a simple $MS^1$ measurement removes the influences of foreign substances (if any), thereby making it possible to obtain image data which reflect the two-dimensional distribution of a fragment (partial structure) originating from a target compound. If a fluorescence microscopic image of a sample fluorescently labelled with a fluorescent dye or similar substance which binds to a specific protein is used, an image showing a highly accurate distribution of that specific protein can be obtained by the process of Step S2. This improves the reliability and accuracy of the comparison of the optical microscopic image with mass spectrometric imaging graphics in regard to the distribution of that specific protein.

Second Embodiment

As described earlier, in the first embodiment, a luminance distribution image in a specific color is extracted from an optical microscopic image which is a colored image. The data forming this luminance distribution image are two-dimensional data, while the original optical microscopic image, which has the luminance distribution for each of the RGB colors (i.e. for each wavelength), is three-dimensional data including the color or wavelength as one of the parameters. Therefore, the system can be configured to perform a statistical analysis process using a multivariable analysis (such as the PLS) on a matrix obtained from each set of the data forming the optical microscopic image (i.e. the luminance distribution data for each of the different colors of RGB) as well as a matrix obtained from mass spectrometric imaging data at each mass-to-charge ratio, to extract a combination of a color or wavelength and a mass-to-charge ratio which show similar distributions.

In this configuration, as in the first embodiment, when analyzing a slice of biological tissue or the like, it is advantageous to use an image obtained by fluorescently labelling the sample as the optical microscopic image of the sample, while using mass spectrometric imaging data obtained by an $MS^n$ measurement with n being equal to or greater than two as the three-dimensional data.

Third Embodiment

Figure 6:
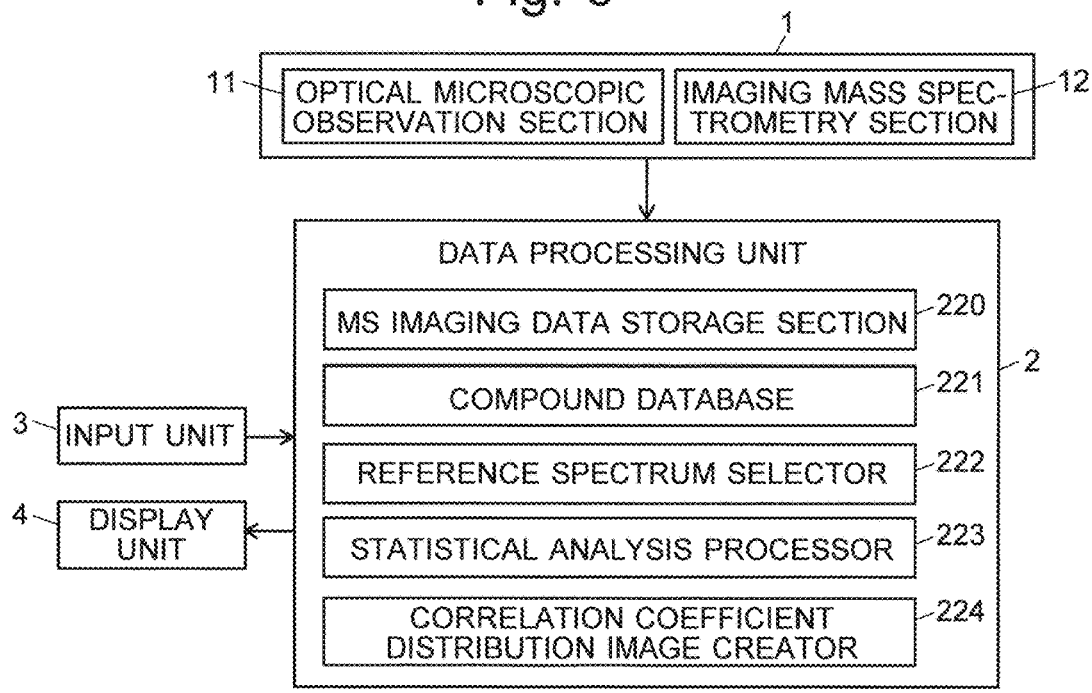
FIG. 6 is a schematic configuration diagram of the third embodiment of an imaging mass microscope system using a data processing device according to the present invention.
Figure 7:
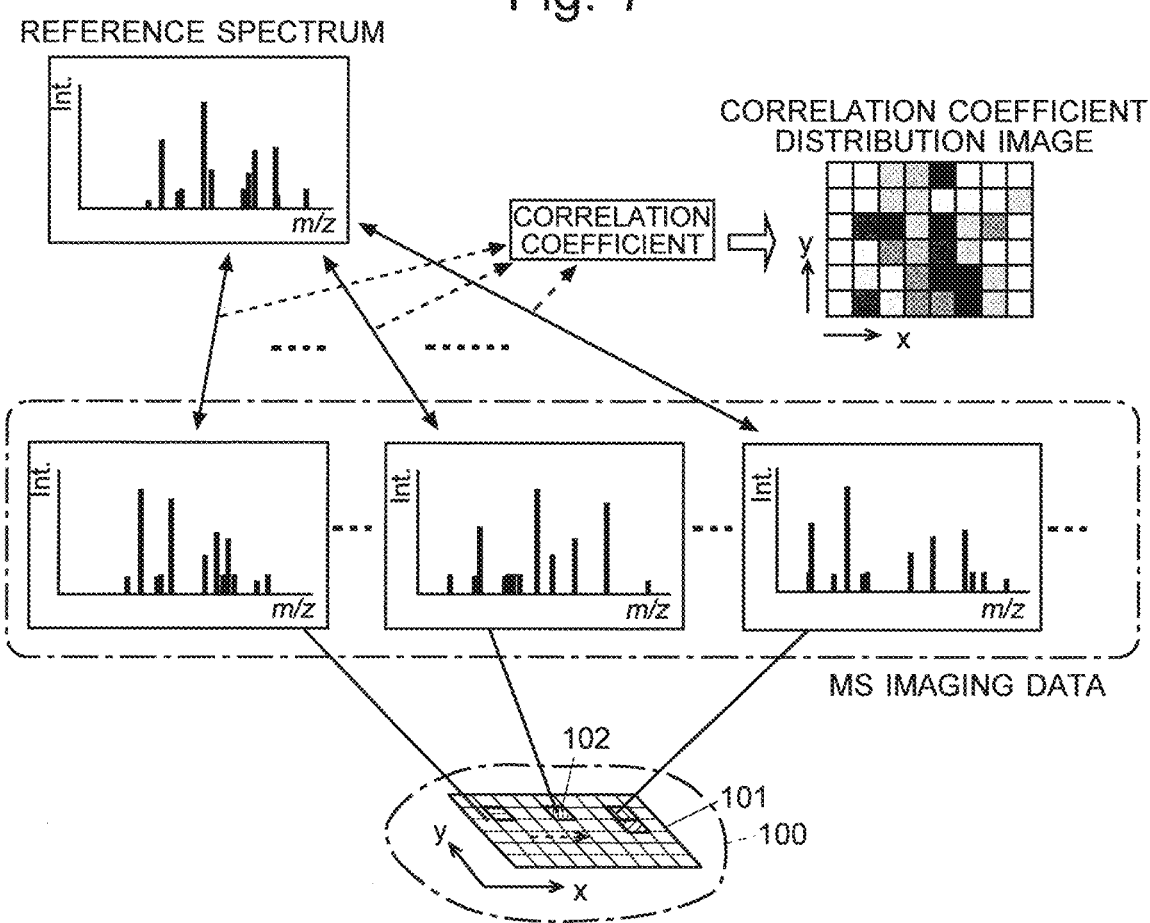
FIG. 7 is a model diagram for explaining the data processing operation in the imaging mass microscope system according to the third embodiment.

FIG. 6 is a schematic configuration diagram of the third embodiment of an imaging mass microscope system using a data processing device according to the present invention. FIG. 7 is a model diagram for explaining the data processing operation in the imaging mass microscope system according to the third embodiment. In FIG. 6, the same components as used in FIG. 1 illustrating the first embodiment are denoted by the same numerals.

The data processing unit 2 in the present system includes the following functional blocks: an MS imaging data storage section 220 for storing mass spectrometric imaging data; a compound database 221 in which mass spectra (which include $MS^n$ spectra) for various known kinds of compounds are registered; a reference spectrum selector 222; a statistical analysis processor 223; and a correlation coefficient distribution image creator 224.

The imaging mass spectrometry section 12 in the imaging mass microscope main unit 1 performs mass spectrometric imaging measurements for a predetermined sample, whereby mass spectrometric imaging data similar to those stored in the MS imaging data storage area 212 in the system of the first embodiment are stored in the MS imaging data storage section 220.

The analysis operator using the input unit 3 specifies a target compound to be observed, such as a compound which is likely to be contained in the sample. Then, the reference spectrum selector 222 accesses the compound database 221, reads a mass spectrum corresponding to the specified compound, and sets this spectrum as the reference spectrum in the statistical analysis processor 223. The statistical analysis processor 223 calculates the correlation coefficient of the signal intensity between one set of mess spectrum data designated as the reference spectrum and one set of mass spectrum data obtained at each pixel and stored in the MS imaging data storage section 220 (see FIG. 7). In other words, the correlation coefficient is calculated for each pixel as the index value which indicates the degree of correlation of the mass spectra. The correlation coefficient distribution image creator 224 converts the value of the correlation coefficient at each pixel into a specific color or gray value according to a color scale or gray scale, for example, and creates an image showing its two-dimensional distribution. This image is displayed on the screen of the display unit 4.

Instead of creating an image showing the distribution of the correlation coefficient by calculating the correlation coefficient between the mass spectra at each pixel, an image which shows the correlation between mass spectra in a two-dimensional form may be created by performing a statistical analysis process using a multivariate analysis, such as the PLS.

A high degree of similarity between the mass spectra means that the same compound is likely to be present. Accordingly, the correlation coefficient distribution image displayed in the previously described manner serves as a two-dimensional distribution image showing the areas in which the target compound specified by the analysis operator is likely to be present.

As for the reference spectrum, a spectrum obtained by processing some data may be used in place of a spectrum which is obtained through a measurement, as with a mass spectrum. Specifically, as described earlier, a factor-loading spectrum which shows the relationship between mass-to-charge ratio and factor loading can be created for each principal component by performing a principal component analysis on mass spectrometric imaging data. The factor-loading spectrum shows partial chemical structures which are similar to each other and present in higher quantities on the entire basis. Based on mass spectrometric imaging data obtained through a measurement for a reference sample, a factor-loading spectrum may be calculated for each principal component and used as the reference spectrum to create a correlation coefficient distribution image in the previously described manner. On this image, an area where compounds with similar partial chemical structures are present in high quantities can be located.

In the third embodiment, as in the first embodiment, mass spectrometric imaging data obtained by an $MS^n$ measurement with n being equal to or greater than two may preferably be used for the processing. For example, consider the case where the distribution of a specific protein needs to be investigated but the influences of foreign substances cannot be sufficiently removed even by the use of $MS^n$ spectra since there is a considerable amount of foreign substances whose mass-to-charge ratios are approximately equal to that of the protein concerned. In such a case, the $MS^n$ spectrum data obtained for each pixel can be used as the mass spectrometric imaging data. By calculating the correlation coefficient of those data with a reference $MS^n$ spectrum for each pixel, or by performing a statistical analysis process using a multivariate analysis, such as the PLS, an image which shows a correlation can be created. The thereby obtained image is barely affected by the foreign substances and highly reliable.

Fourth Embodiment

Figure 8:
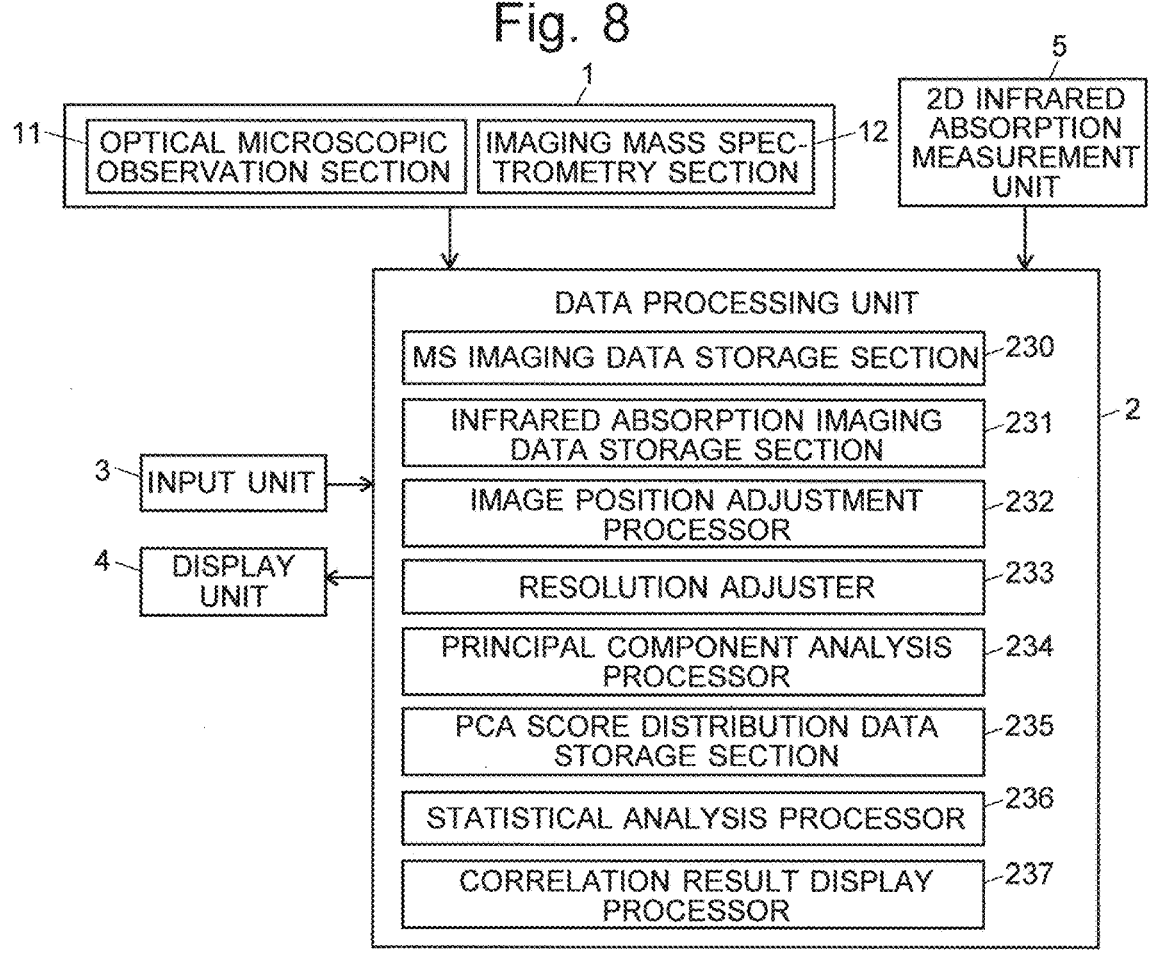
FIG. 8 is a schematic configuration diagram of the fourth embodiment of an imaging mass microscope system using a data processing device according to the present invention.
Figure 9:
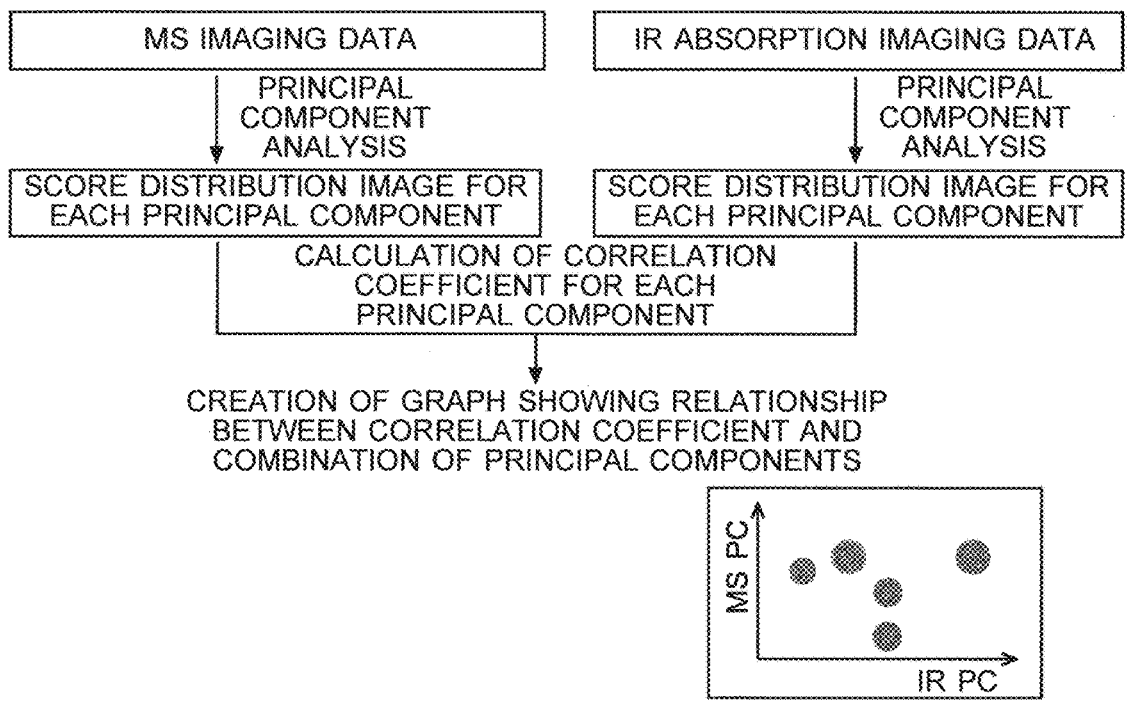
FIG. 9 is a model diagram for explaining the data processing operation in the imaging mass microscope system according to the fourth embodiment.

FIG. 8 is a schematic configuration diagram of the fourth embodiment of an imaging mass spectroscope system using a data processing device according to the present invention. FIG. 9 is a model diagram for explaining the data processing operation in the imaging mass microscope system according to the fourth embodiment. In FIG. 8, the same components as used in FIG. 1 illustrating the first embodiment are denoted by the same numerals.

The present system includes a two-dimensional infrared absorption measurement unit 5 for measuring the distribution of the infrared absorbance within a two-dimensional area on a sample, as a measurement unit apart from the imaging mass microscope main unit 1. The two-dimensional infrared absorption measurement unit 5 includes an optical system of an infrared microscope, a linear array detector, and a sample drive mechanism for driving the sample in a direction orthogonal to the extending direction of the array of the detector, with these elements combined together so that an infrared absorption spectrum can be obtained at each of the micro areas formed by subdividing a predetermined two-dimensional area on a sample.

The data processing unit 2 includes the following functional blocks: an MS imaging data storage section 230 for storing mass spectrometric imaging data; an infrared absorption imaging data storage section 231 for storing infrared absorption imaging data which include infrared absorption spectrum data collected for each micro area; an image position adjustment processor 232; a resolution adjuster 233; a principle component analysis processor 234; a PCA score distribution data storage section 235; a statistical analysis processor 236; and a correlation result display processor 237.

The imaging mass spectrometry section 12 in the imaging mass microscope main unit 1 performs mass spectrometric imaging measurements for a predetermined sample, whereby mass spectrometric imaging data similar to those stored in the MS imaging data storage area 212 in the system of the first embodiment are stored in the MS imaging data storage section 230. Additionally, the two-dimensional infrared absorption measurement unit 5 performs infrared absorption imaging measurements for the same area on the same sample, whereby infrared absorption spectrum data over a predetermined wavelength range are obtained for each micro area and stored in the infrared absorption imaging data storage section 231.

When an analysis operator using the input unit 3 enters a command to initiate the process, the image position adjustment processor 232 and the resolution adjuster 233 perform the image position adjustment process and the resolution adjustment process on the MS imaging data and the infrared absorption imaging data in a manner similar to the image position adjustment processor 23 and the resolution adjuster 24 in the first embodiment. One or both of these processes may be omitted if they are unnecessary. The principal component analysis processor 234 performs a principal component analysis on each of the MS imaging data and infrared absorption imaging data which have undergone the image position adjustment process and the resolution adjustment process. The principal component analysis yields a score value for each pixel as well as for each principal component. The score values are stored in the PCA score distribution data storage section 235.

The statistical analysis processor 236 reads, from the storage section 235, distribution data of the score values for one principal component based on the MS imaging data as well as distribution data of the score values for one principal component based on the infrared absorption imaging data, correlates the score values for each pair of the corresponding pixels, and calculates the correlation coefficient. For example, it determines the spatial correlation between the distribution data of the score values for the first principal component based on the MS imaging data and those of the score values for the first principal component based on the infrared absorption imaging data, and calculates the correlation coefficient. The correlation coefficient is similarly calculated for every possible combination of the principal components. The correlation result display processor 237 creates a graph and displays it on the screen of the display unit 4. FIG. 9 shows one example of the graph, in which the correlation coefficients are represented by circles within a frame whose horizontal axis represents the principal components based on the infrared absorption imaging data (IR PC) while its vertical axis represents the principal components based on the MS imaging data (MS PC), with each circle indicating the sign of the correlation coefficient by its color and the magnitude of the absolute value of the correlation coefficient by its size.

By viewing the display, the analysis operator can visually recognize which principal components show similar distributions of the score value in the mass spectrometric imaging measurement and the infrared absorption imaging measurement. This allows the analysis operator, for example, to compare factor-loading spectra corresponding to the highly correlated principal components, and find a combination of the mass-to-charge ratio and the infrared absorption wavelength having high factor-loading values. Thus, the target compound can be identified from both mass-to-charge ratio and absorption wavelength.

Needless to say, such an analysis is not limited to the combination of the mass spectrometric imaging measurement and the infrared absorption imaging measurement; it can be similarly applied to any measurement in which a set of data dependent on a predetermined parameter can be obtained for each micro area within the same two-dimensional area on a sample.

Fifth Embodiment

Figure 10:
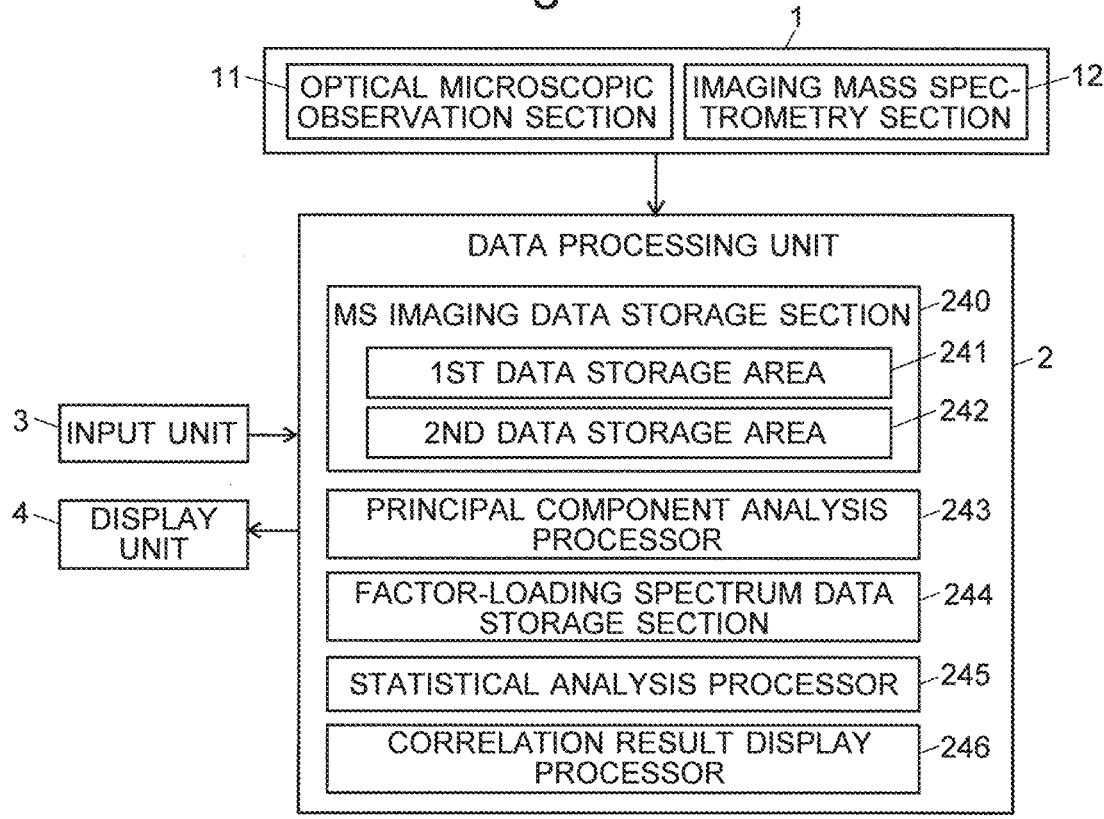
FIG. 10 is a schematic configuration diagram of the fifth embodiment of an imaging mass microscope system using a data processing device according to the present invention.
Figure 11:
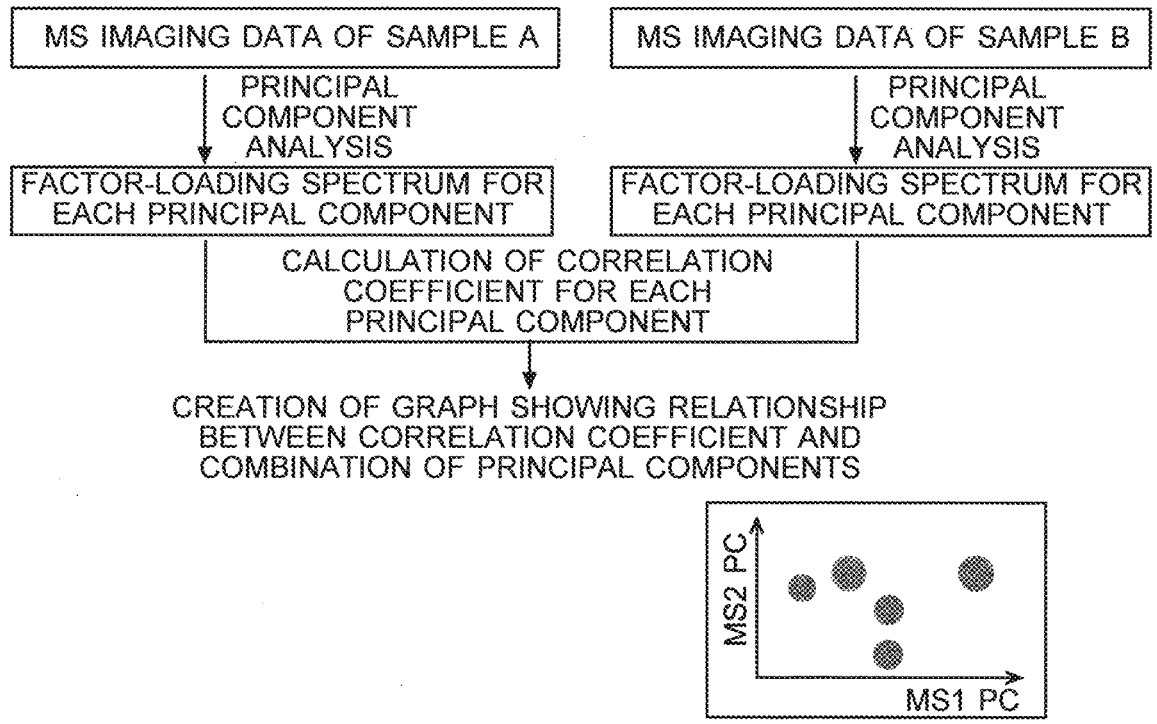
FIG. 11 a model diagram for explaining the data processing operation in the imaging mass microscope system according to the fifth embodiment.
Figure 15C:
FIGS. 15C through 15E are distribution images of the score values for each principal component obtained by performing a principal component analysis on the original image.
Figure 15D:
Figure 15E:
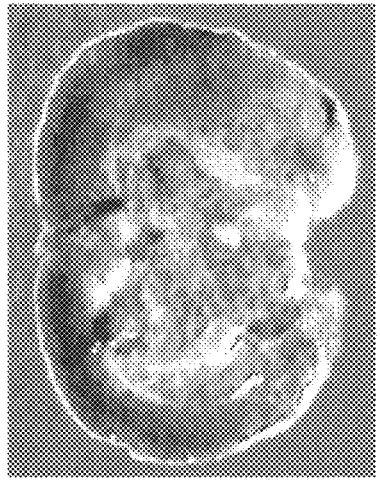
Figure 15A:
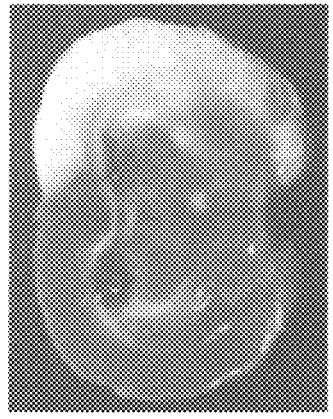
FIG. 15A is an original optical microscopic image.
Figure 15B:
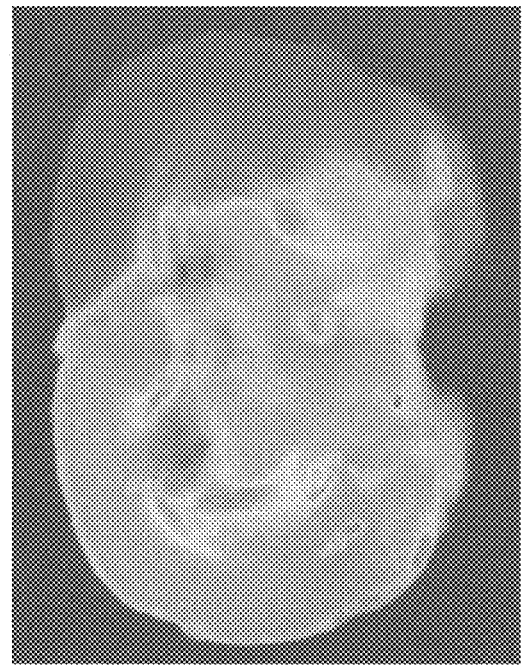
FIG. 15B is a false-color composite image created from those distribution images.

FIG. 10 is a schematic configuration diagram of the fifth embodiment of an imaging mass microscope system using a data processing device according to the present invention. FIG. 11 a model diagram for explaining the data processing operation in the imaging mass microscope system according to the fifth embodiment. In FIG. 10, the same components as used in FIG. 1 illustrating the first embodiment are denoted by the same numerals.

The data processing unit 2 includes the following functional blocks: an MS imaging data storage section 240 for storing mass spectrometric imaging data; a principal component analysis processor 243; a factor-loading spectrum storage section 244; a statistical analysis processor 245; and a correlation result display processor 246. The MS imaging data storage section 240 includes a first data storage area 241 and a second data storage area 242 in each of which a set of MS imaging data can be independently stored.

In the present system, the imaging mass microscope main unit 1 performs a mass spectrometric imaging measurement for each of the two different samples (which are hereinafter called samples "A" and "B"), whereby two sets of mass spectrometric imaging data are respectively stored in the first and second data storage areas 241 and 242 of the MS imaging data storage section 240. The samples A and B may be two different areas on the same sample. It is assumed that the number of pixels is the same in the measurements for both samples A and B.

When an analysis operator using the input unit 3 enters a command to initiate the process, the principal component analysis processor 234 reads the MS imaging data for the respective samples A and B from the storage section 240 and performs a principal component analysis on each set of MS imaging data. In each principal component analysis, a factor-loading spectrum as described earlier is obtained for each principal component and stored in the factor-loading spectrum storage section 244.

The statistical analysis processor 245 reads, from the storage section 244, a factor-loading spectrum for one principal component based on the MS imaging data of sample A as well as a factor-loading spectrum for one principal component based on the MS imaging data of sample B, correlates the factor loadings for each pair of the corresponding mass-to-charge ratios, and calculates the correlation coefficient. For example, it determines the correlation in mass-to-charge ratio between the factor-loading spectrum for the first principle component based on the MS imaging data of sample A and the factor-loading spectrum for the first principle component based on the MS imaging data of sample B, and calculates the correlation coefficient. The correlation coefficient is similarly calculated for every possible combination of the principal components. The correlation result display processor 246 creates a graph and displays it on the screen of the display unit 4. FIG. 11 shows one example, in which the correlation coefficients are represented by circles within a frame whose horizontal axis represents the principal components based on the MS imaging data of sample B (MS2 PC) while its vertical axis represents the principal components based on the MS imaging data of sample A (MS1 PC), with each circle indicating the sign of the correlation coefficient by its color and the magnitude of the absolute value of the correlation coefficient by its size.

By viewing the display, the analysis operator can visually recognize which principal components have similar factor-loading spectra in the mass spectrometric imaging measurement performed on different samples. This allows the analysis operator, for example, to compare the spatial distributions of the respective score values of the highly correlated principal components, and recognize the state of distribution of the same compound on the different samples or that of different compounds having similar chemical structures.

Needless to say, such an analysis is not limited to the mass spectrometric imaging measurement; it can be similarly applied to any measurement in which a set of data dependent on a predetermined parameter can be obtained for each micro area within the same two-dimensional area on a sample.

It should be noted that any of the previously described embodiments is a mere example of the present invention, and any change, modification, addition or the like appropriately made within the spirit of the present invention in any aspects other than those already described will evidently fall within the scope of claims of the present application.

REFERENCE SIGNS LIST

1 . . . Imaging Mass Microscope Main Unit
11 . . . Optical Microscopic Observation Section
12 . . . Imaging Mass Spectrometry Section
2 . . . Data Processing Unit
21 . . . Data Storage Section
211 . . . Optical Microscopic Image Data Storage Area
212 . . . MS Imaging Data Storage Area
22 . . . Optical Microscopic Image Feature Extractor
23, 232 . . . Image Position Adjustment Processor
24, 233 . . . Resolution Adjuster
25, 223, 236, 245 . . . Statistical Analysis Processor
26 . . . Analysis Result Display Processor
220, 230, 240 . . . MS Imaging Data Storage Section
231 . . . Infrared Absorption Imaging Data Storage Section
221 . . . Compound Database
222 . . . Reference Spectrum Selector
224 . . . Correlation Coefficient Distribution Image Creator
234, 243 . . . Principle Component Analysis Processor
235 . . . PCA Score Distribution Data Storage Section
237, 246 . . . Correlation Result Display Processor
241 . . . First Data Storage Area
242 . . . Second Data Storage Area
244 . . . Factor-Loading Spectrum Storage Section
3 . . . Input Unit
4 . . . Display Unit
5 . . . Two-Dimensional Infrared Absorption Measurement Unit

The invention claimed is:

1. A data processing device for processing sample spectrum data obtained for each of a plurality of micro areas within a two-dimensional area on a sample and reference spectrum data provided as a reference, to obtain information on the sample, the data processing device comprising:
a) a statistical analysis processor for performing, for each of the micro areas, a statistical analysis process on the sample spectrum data corresponding to the micro area and the reference spectrum data, to calculate an index value indicating a degree of similarity or difference between spectra; and
b) an image creator for creating an image showing a two-dimensional distribution of the index value corresponding to the two-dimensional area on the sample, based on the index value obtained for each of the micro areas by the statistical analysis processor.

2. The data processing device according to claim 1, wherein:
the sample spectrum data and the reference spectrum data are mass spectrum data obtained by an $MS^n$ measurement with n being equal to or greater than two.

3. The data processing device according to claim 1, wherein the image creator creates the image according to at least one of a color scale or a gray scale based on the index value.

4. The data processing device according to claim 1, further comprising a reference spectrum selector configured to set the reference spectrum data.

5. The data processing device according to claim 4, further comprising a compound database;
wherein the reference spectrum selector is configured to access the compound database to read a mass spectrum corresponding to the reference spectrum data.

6. The data processing device according to claim 1, further comprising an input unit configured to allow an operator to specify a target compound to be observed.

7. The data processing device according to claim 2, further comprising an input unit configured to allow an operator to specify a target compound to be observed.

8. The data processing device according to claim 3, further comprising an input unit configured to allow an operator to specify a target compound to be observed.

9. The data processing device according to claim 4, further comprising an input unit configured to allow an operator to specify a target compound to be observed.

10. The data processing device according to claim 5, further comprising an input unit configured to allow an operator to specify a target compound to be observed.

11. The data processing device according to claim 1, further comprising a display unit configured to display the image showing the two-dimensional distribution of the index value corresponding to the two-dimensional area on the sample.

12. The data processing device according to claim 1, wherein the reference spectrum data is a spectrum data of a known kind of substance.

* * * * *